United States Patent
Verma et al.

(10) Patent No.: US 10,180,384 B2
(45) Date of Patent: Jan. 15, 2019

(54) AUTOMATED HEPA FILTER INTEGRITY TESTING

(71) Applicant: Mallinckrodt Nuclear Medicine LLC, Maryland Heights, MO (US)

(72) Inventors: Sumit Verma, Chesterfield, MO (US); Bryan S. Petrofsky, St. Louis, MO (US); Kevin B. Graves, Catawissa, MO (US); Donald W. Reese, Florissant, MO (US)

(73) Assignee: Mallinckrodt Nuclear Medicine LLC, Maryland Heights, MO (US)

( * ) Notice: Subject to any disclaimer, the term of this patent is extended or adjusted under 35 U.S.C. 154(b) by 100 days.

(21) Appl. No.: 15/409,000

(22) Filed: Jan. 18, 2017

(65) Prior Publication Data

US 2018/0031466 A1    Feb. 1, 2018

Related U.S. Application Data

(60) Provisional application No. 62/369,502, filed on Aug. 1, 2016.

(51) Int. Cl.
| | | |
|---|---|---|
| *B01D 35/143* | (2006.01) | |
| *B01D 46/00* | (2006.01) | |
| *B01D 65/10* | (2006.01) | |
| *G01N 15/08* | (2006.01) | |
| *G21F 7/015* | (2006.01) | |

(52) U.S. Cl.
CPC ....... *G01N 15/0806* (2013.01); *B01D 65/102* (2013.01); *B01D 65/104* (2013.01); *G01N 15/082* (2013.01); *G21F 7/015* (2013.01); *B01D 46/0086* (2013.01); *B01D 2273/18* (2013.01); *G01N 2015/084* (2013.01)

(58) Field of Classification Search
CPC .. B01D 35/143; B01D 46/00; B01D 46/0086; B01D 65/10; B01D 65/102; B01D 65/104; B01D 2273/18; G01N 15/08; G01N 15/0806; G01N 15/082; G01N 15/084; G21F 1/015
See application file for complete search history.

(56) References Cited

U.S. PATENT DOCUMENTS

| | | |
|---|---|---|
| 4,494,403 A | 1/1985 | Bowers et al. |
| 4,515,007 A | 5/1985 | Herman |

(Continued)

FOREIGN PATENT DOCUMENTS

| | | | |
|---|---|---|---|
| EP | 1057515 A1 | 12/2000 | |
| WO | 2016057266 A1 | 4/2016 | |
| WO | WO 2017216316 A1 * | 12/2017 | ......... B01D 46/0086 |

OTHER PUBLICATIONS

International Search Report and Written Opinion of the International Search Authority regarding PCT/US2017/013941 dated May 16, 2017; pp. 14.

*Primary Examiner* — Nguyen Ha
(74) *Attorney, Agent, or Firm* — Armstrong Teasdale LLP (57) ABSTRACT

HEPA filter integrity testing apparatus including an automated mover, a scan module connected to the automated mover, and scan probes disposed along the length of the scan module. Assemblies also include HEPA filters and the filter integrity testing apparatus. A method of determining the integrity of HEPA filters with the filter integrity apparatus is disclosed.

19 Claims, 4 Drawing Sheets

(56) References Cited

U.S. PATENT DOCUMENTS

| | | | | |
|---|---|---|---|---|
| 7,010,960 B1* | 3/2006 | Grantham | ............... | G01M 3/00 |
| | | | | 73/40 |
| 8,549,895 B2 | 10/2013 | Chung et al. | | |
| 2006/0272301 A1 | 12/2006 | Morse et al. | | |
| 2008/0210000 A1* | 9/2008 | Yoshitome | .............. | F24F 3/161 |
| | | | | 73/198 |
| 2010/0116031 A1* | 5/2010 | Xu | .................... | G01N 15/0625 |
| | | | | 73/38 |
| 2014/0115852 A1* | 5/2014 | Morse | ................ | B01D 46/0091 |
| | | | | 29/402.08 |
| 2016/0097705 A1 | 4/2016 | Woolard | | |

\* cited by examiner

AUTOMATED HEPA FILTER INTEGRITY TESTING

CROSS-REFERENCE TO RELATED APPLICATION

This application claims priority to U.S. Provisional Application Ser. No. 62/369,502 filed on Aug. 1, 2016, which is incorporated herein in its entirety.

FIELD

The field of the disclosure relates generally to automated HEPA filter integrity testing systems and methods, to automated HEPA filter integrity testing systems and methods for operation in radionuclide generator hot cells and isolators.

BACKGROUND

Shielded nuclear containment chambers, referred to as hot cells or isolators, are used in the radiopharmaceutical and nuclear energy industries to protect personnel from the radioactive material contained therein and radiation emitted therefrom. As used herein, hot cells and isolators are collectively referred to as isolators. In the radiopharmaceutical industry, radioactive material used for diagnostic and therapeutic purposes may be produced using a radionuclide generator, such as column housed in an isolator. Additionally, associated radionuclide process equipment is typically housed in an isolator.

Air filters such as HEPA filters are used to provide pharmaceutical grade sterile filtered air to isolators. Typically, one or more HEPA filters are mounted in the ceiling of the isolator. For instance, four HEPA filters may be used in a 2×2 matrix.

The integrity of each HEPA filter must be certified regularly by challenging the integrity of the full filter HEPA membrane surface, as well as any associated filter frame housing gaskets and/or seals (e.g. gel seals). Filter integrity testing is typically performed manually by introducing an aerosol such as dispersed oil particulate "DOP" or a poly alpha olefin ("PAO") aerosol from the inlet filter plenum, and checking for leakage of this aerosol through the filter or housing at the filter outlet. Typically, an operator moves a hand-held scanning probe in overlapping strokes across every square inch of the HEPA filter face and seal, keeping the probe a maximum distance of about 2.5 cm from the filter face at all times, and moving no faster than about 3 meters per minute. The probe draws a continuous air sample during this scanning process that is monitored for presence of aerosol. If aerosol is detected, an alarm sounds and the operator stops and investigates.

Radionuclide isolator HEPA filter scanning by known methods may be problematic for a number of reasons. For instance, filter access is difficult within small isolators. Further, process equipment and/or processing sequence may block, impair or limit interior access. Further, delicate HEPA filter membrane may be damaged if a hand-held probe contacts the filter face during manual scanning. Yet further, manual movement rate and probe distance from the filter face is difficult to gauge and is inconsistent. Moreover, it is difficult to certify that sequential manual strokes overlap thereby assuring that the entire filter face has been scanned. Still further, the time required to test filter media may present unsafe radiation and/or hazardous chemical exposure conditions for the testing personnel. Yet further, isolators often utilize a diffusion grid or membrane situated between the HEPA filters and the isolator working volume in order to create a full ceiling HEPA filtered unidirectional airflow. Such diffusion grids or membranes must be manually removed in order to access HEPA filters and perform HEPA filter certification and then reinstalled after certification is complete. Manually handling diffusion grids or membranes can cause damage to filters and the grids/membranes, and thereby increase testing time and concomitant process cycle time. A need therefore exists for improved HEPA filter integrity testing systems and methods.

This Background section is intended to introduce the reader to various aspects of art that may be related to various embodiments and aspects of the present disclosure, which are described and/or claimed below. This discussion is believed to be helpful in providing the reader with background information to facilitate a better understanding of the various embodiments and aspects of the present disclosure. Accordingly, it should be understood that these statements are to be read in this light, and not as admissions of prior art.

SUMMARY

In one aspect, the disclosure relates to a filter integrity testing apparatus. The filter integrity testing apparatus comprises: (A) an automated mover; (B) a scan module having a length and connected to the automated mover, the automated mover operable to move the scan module along an axis of travel, wherein the scan module length extends substantially perpendicular to the direction of travel; and (C) a plurality of scan probes disposed along the length of the scan module. Each scan probe includes a gas receiving end and a gas discharge end. Each scan probe is similarly oriented with respect to the gas receiving end and the gas discharge end, and the gas receiving end of each scan probe overlaps a gas receiving end of each adjacent scan probe. Each scan probe has a length extending substantially perpendicular to the axis of travel.

In another aspect, the disclosure relates to an assembly comprising at least one HEPA filter mounted in a filter housing assembly, the HEPA filter having (i) a face defined by four edges and having a rectangular shape, (ii) a first edge of the face and a second edge of the face define a length of the HEPA filter face, and (iii) a third edge of the face and a fourth edge of the face define a width of the HEPA filter face. The assembly further comprises a filter integrity testing apparatus comprising (i) an automated mover, (ii) a scan module having a length and connected to the automated mover, the automated mover operable to move the scan module along an axis of travel, wherein the scan module length extends substantially perpendicular to the direction of travel, and (iii) a plurality of scan probes disposed along the length of the scan module. Each scan probe includes a gas receiving end and a gas discharge end wherein each scan probe is similarly oriented with respect to the gas receiving end and the gas discharge end, and the gas receiving end of each scan probe overlaps a gas receiving end of each adjacent scan probe. Each scan probe has a length extending substantially perpendicular to the axis of travel, and wherein the automated mover defines a first end having a face and a second end having a face wherein a first mount is connected to the automated mover first end face and a second mount is connected to the second end face. The filter integrity testing apparatus is coupled to the filter housing assembly by the first mount and the second mount. The scan module is configured to sweep the complete length and width of the at least one HEPA filter face with the gas receiving ends of the plurality of scan probes.

In still another aspect, a method of determining the integrity of a HEPA filter comprises introducing a challenge aerosol upstream from a first face of at least one HEPA filter, the HEPA filter having (i) a face defined by four edges and having a rectangular shape, (ii) a first edge of the face and an associated gasket and/or seal and a second edge of the face and an associated gasket and/or seal define a length of the HEPA filter face, and (iii) a third edge of the face and an associated gasket and/or seal and a fourth edge of the face and an associated gasket and/or seal define a width of the HEPA filter face. The method further comprises a second step of analyzing the opposite face of the at least one HEPA filter for integrity with a filter integrity testing apparatus comprising (i) an automated mover, (ii) a scan module having a length and connected to the automated mover, the automated mover operable to move the scan module along an axis of travel, wherein the scan module length extends substantially perpendicular to the direction of travel, and (iii) a plurality of scan probes disposed along the length of the scan module. Each scan probe includes a gas receiving end and a gas discharge end, each scan probe is similarly oriented with respect to the gas receiving end and the gas discharge end, and the gas receiving end of each scan probe overlaps a gas receiving end of each adjacent scan probe. Each scan probe has a length extending substantially perpendicular to the axis of travel. The scan module is configured such that the plurality of scan probes sweep the entire length and width of the HEPA filter face and associated gasket and/or seal. The method further comprises a third step of selecting a scan probe and a fourth step of moving the scan module across the entire HEPA filter face at a controlled rate sweeping the complete length of said face while continuously collecting gas samples therefrom with the selected scan probe receiving end and analyzing collected samples for the presence of aerosol with an aerosol detection apparatus operably connected to the scan probe gas discharge end to determine the integrity of a HEPA filter. The method further comprises a fifth step of deselecting the selected scan probe and selecting a scan probe that was not previously selected, and repeating the fourth step. The method further comprises a sixth step of repeating the fifth step until all scan probes have been selected.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Corresponding reference characters indicate corresponding parts throughout the Figures.

DETAILED DESCRIPTION

Radioactive material is used in nuclear medicine for diagnostic and therapeutic purposes by injecting a patient with a small dose of the radioactive material, which concentrates in certain organs or regions of the patient. Radioactive materials typically used for nuclear medicine include Technetium-99m ("Tc-99m"), Iodine-131 ("I-131") and Thallium-201.

Some radioactive materials, like Tc-99m, may be produced using a radionuclide generator. Radionuclide generators generally include a column that has media for retaining a long-lived parent radionuclide that spontaneously decays into a daughter radionuclide that has a relatively short half-life. The column may be incorporated into a column assembly that has a needle-like outlet port that receives an evacuated vial to draw saline or other eluent liquid, provided to a needle-like inlet port, through a flow path of the column assembly, including the column itself. This liquid may elute and deliver daughter radionuclide from the column and to the evacuated vial for subsequent use in nuclear medical imaging applications, among other uses.

Radionuclide generators are enclosed within an isolator that includes an enclosure constructed of nuclear radiation shielding material designed to shield the surrounding environment from nuclear radiation. Suitable shielding materials from which isolators may be constructed include, for example and without limitation, lead, depleted uranium, and tungsten. In some embodiments, isolators are constructed of steel-clad lead walls forming a cuboid or rectangular prism. In some embodiments, an isolator may include a viewing window constructed of a transparent shielding material. Suitable materials from which viewing windows may be constructed include, for example and without limitation, lead glass.

Isolator pressure may be controlled at a negative or positive pressure relative to the surrounding environment and/or relative to adjacent process equipment. In some embodiments, the isolator pressure is controlled at negative pressure, such as from about −0.01 inches $H_2O$ to about −0.15 in$H_2O$.

HEPA filters are used to provide pharmaceutical grade sterile filtered air to isolators. In some embodiments, air supply HEPA filters are positioned in a filter housing assembly in the ceiling portion of the isolator and provide for a generally uniform and unidirectional flow of filtered air over the area of the isolator. In some other embodiments, the isolator air supply further comprises a diffusion grid or membrane positioned between the outlet side of the HEPA filters and the isolator working volume thereby forming a plenum that provides for improved air distribution as compared to HEPA filters alone. Such a diffusion grid or membrane must be removed to access the HEPA filters for inspection and servicing.

Figure 1:
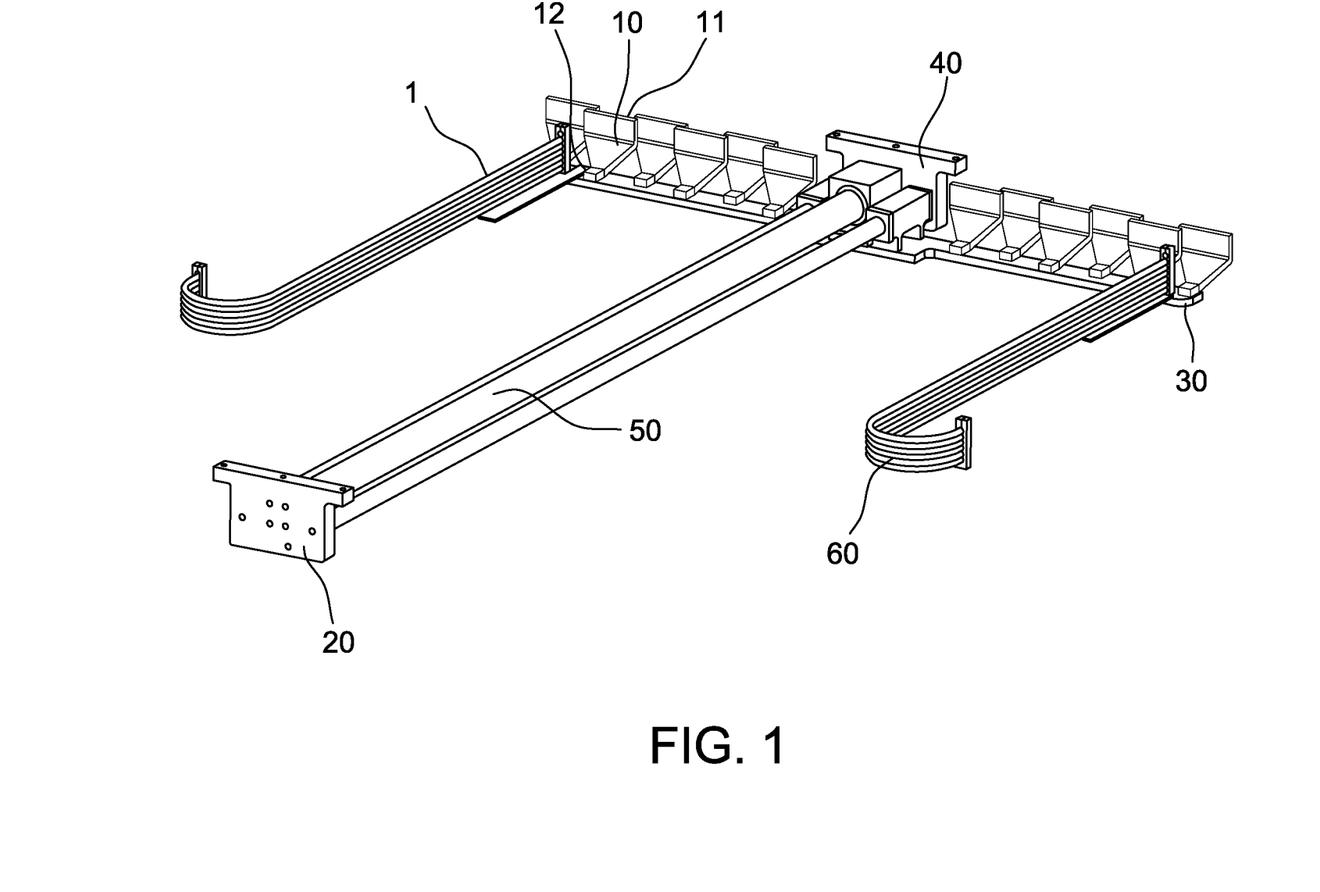
FIG. 1 is a perspective view of a portion of a filter integrity testing apparatus.

FIG. 1 is a perspective view of one embodiment of a filter integrity testing apparatus 1 of the present disclosure. As shown, the apparatus 1 generally comprises a scan module 30 including a plurality of scan probes 10 connected to an automated mover 50.

As further shown in FIG. 1, scan module 30 has a length having a plurality of separate scan probes 10 disposed at discrete points along its length. Each scan probe 10 includes a gas receiving end 11 and a gas discharge end 12. The gas receiving end 11 comprises a port defining a length. The gas discharge end 12 is suitably coupled to one end of an air suction line 60 such that the gas discharge end and air suction line are operably connected. The other end of the air suction line 60 is operably connected to an aerosol detection apparatus. The air suction lines are flexible and extendable with scan module 30 movement. Each scan probe is similarly oriented with respect to the gas receiving open end and the gas discharge open end such that, during integrity testing, the HEPA filter face is scanned with the gas receiving end of each scan probe 10. Each scan probe 10 has a length extending substantially perpendicular to the axis of travel. The scan probes 10 are arranged on the length of the scan module 30 such that the length of each gas intake port overlaps the gas intake port of each adjacent scan probe 10. Overlap of gas intake ports may suitably be about 0.25 cm, or at least about 0.25 cm, about 0.5 cm or about 0.75 cm, wherein the overlap provides for complete coverage of scanned surfaces.

Figure 3:
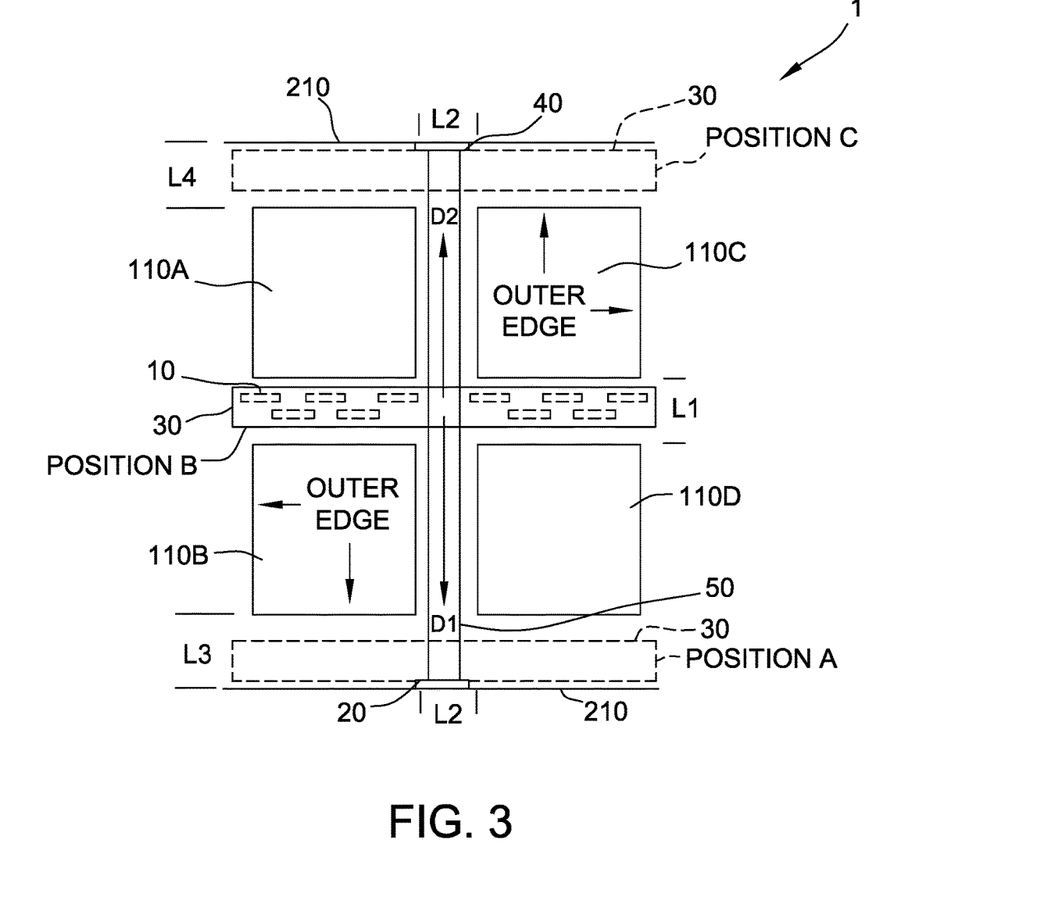
FIG. 3 is a plan view of a filter integrity apparatus mounted to an isolator HEPA filter assembly.
Figure 4:
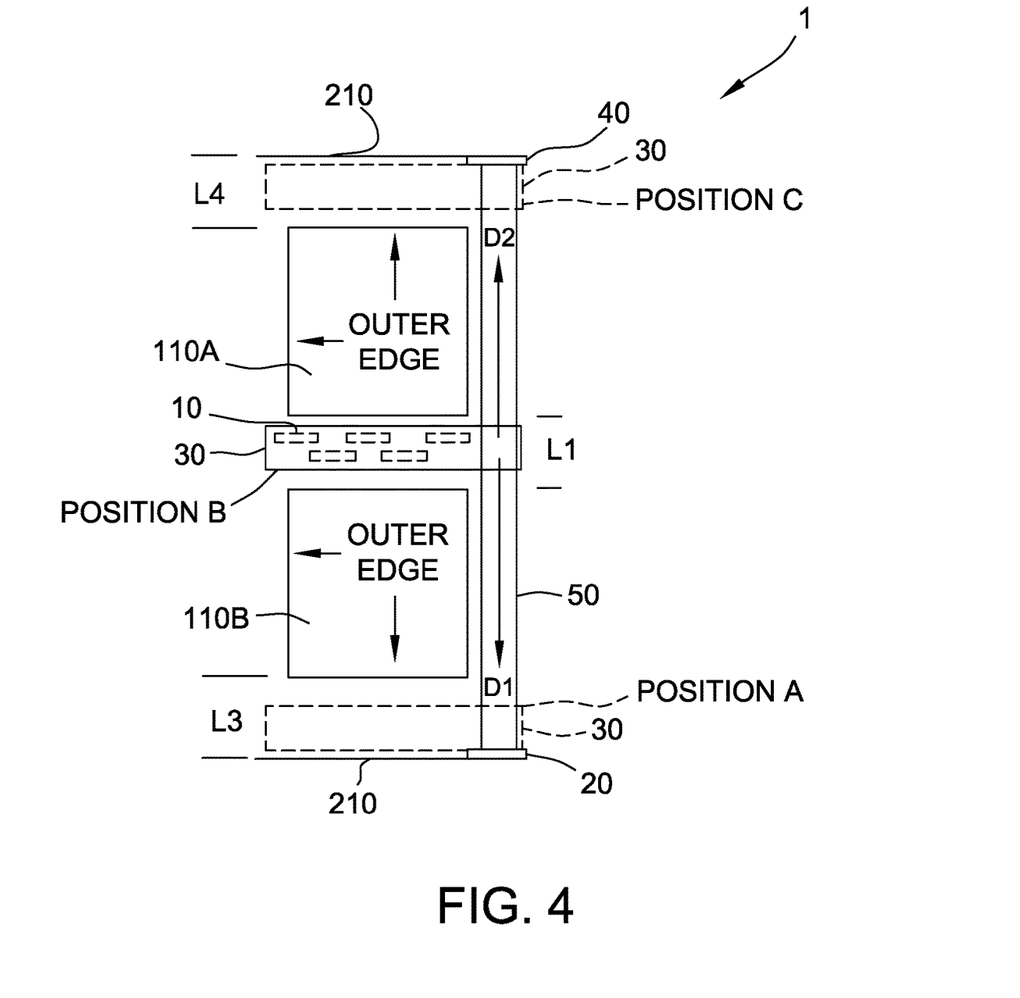
FIG. 4 is a plan view of a filter integrity apparatus mounted to an isolator HEPA filter assembly in a 2×1 filter grid arrangement.

As further depicted in FIG. 1, automated mover 50 defines a first end having a first end face 20 and a second end having a second end face 40. Automated mover 50 comprises a first mount coupled to the first end face 20 and a second mount coupled to the second end face 40. The first and second mounts provide an attachment for connecting or coupling (e.g., bolting) the filter integrity testing apparatus 1 to an isolator structural support. The automated mover 50 is controllably operable to move the scan module in an axis of travel comprising a first direction of travel toward the first end face and a second direction of travel essentially 180° opposed to the extension direction of travel and toward the second end face such as depicted in FIGS. 3 and 4 as directions D1 and D2, respectively. As depicted in FIGS. 3 and 4, the length of the scan module 30 having the scan probes 10 disposed thereon is oriented such that the entire filter face and sealed outer edges are covered by the scan probes during a scan. In some embodiments, the scan module is oriented essentially perpendicular to the automated mover 50, and substantially perpendicular to the first direction of travel, D1, and the second direction of travel, D2, as depicted in FIGS. 3 and 4.

Automated mover 50 is operable by any mechanism or system suitable for controllably moving the scan module 30 across the face of one or more HEPA filters. In some embodiments the automated mover 50 is suitably a pneumatically actuated cylinder, such as a rodless cylinder as known in the art. In some such embodiments, the rodless cylinder comprises a driving member disposed in a housing, wherein the cylinder is provided with control ports for controlling the direction of movement axially within the housing. In such embodiments, the scan module 30 movement rate and position is controlled by gas (e.g., air or nitrogen) or liquid (hydraulic fluid) flow regulation to the cylinder. In some embodiments the automated mover 50 is suitably a motor-driven ball-screw apparatus as known in the art. In such embodiments, the scan module 30 movement rate and position is controlled by motor speed regulation.

Figure 2:
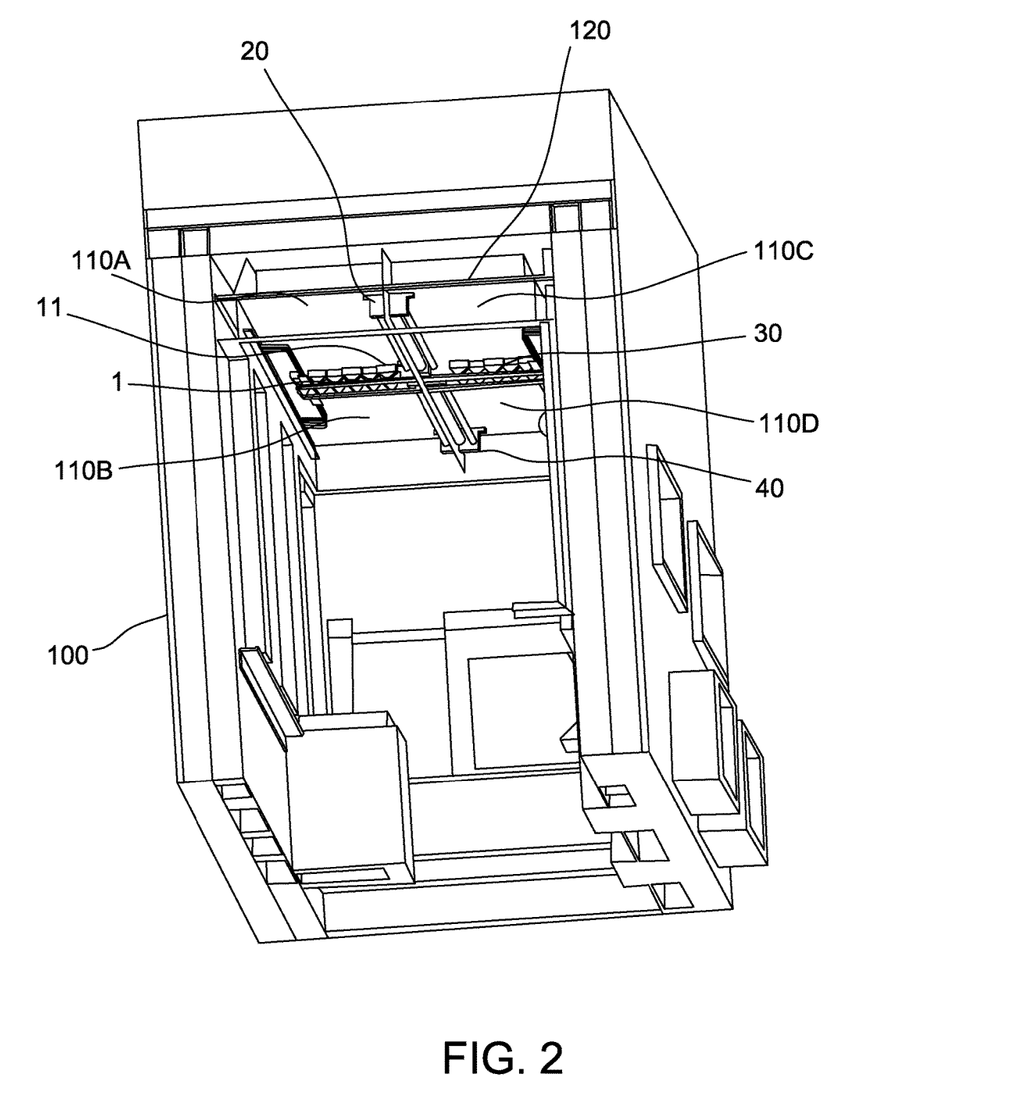
FIG. 2 is a perspective view of the filter integrity apparatus mounted to an isolator HEPA filter assembly.

FIG. 2 is a perspective view of a filter integrity apparatus 1 having a first end face 20 and a second end face 40 mounted to an isolator 100 HEPA filter assembly 120 containing a 2×2 matrix of four HEPA filters 110A, 110B, 110C and 110D wherein the scan module 30 is in a resting position between rows of HEPA filters. The filter integrity testing apparatus 1 is coupled to the filter assembly 120 by the first mount and the second mount described elsewhere herein. In isolator embodiments directed to a diffusion grid or membrane (not depicted) positioned between the outlet side of the HEPA filters and the isolator working volume, the filter integrity apparatus 1 is mounted in the volume between the HEPA filter outlet face and the diffusion grid/membrane. Such an arrangement allows for HEPA integrity testing without removal of the diffusion grid/membrane. Each of the scan probe gas receiving ends 11 are oriented to a position of no more than about 2.5 cm, such as about 1 cm, about 1.5 cm, about 2 cm or about 2.5 cm, above the HEPA filter face.

In some non-limiting example embodiments, the HEPA filter assembly contains a 4×2 matrix (two columns and four rows or two rows and four columns) of HEPA filters (not depicted), a 3×2 matrix (three rows and two columns or three columns and two rows) of HEPA filters (not depicted), a 2×1 matrix of HEPA filters (depicted in FIG. 4) or a single HEPA filter (not depicted). Each HEPA filter comprises a face defined by four edges and having a square or rectangular shape. Each HEPA filter has: (i) a first edge defining a first end of the face and a second edge defining a second edge of the face wherein the first edge and the second edge define a length of the HEPA filter face with respect to the direction of movement of the scan module 30, wherein the scan module moves along the length of the face; and (2) a third edge of the face and a fourth edge of the face wherein the third edge and the fourth edge define a width of the HEPA filter face wherein the length of the scan module is greater than the width of the HEPA filter face. The scan module 30 is configured to sweep the complete length and width of the HEPA filter face and any associated gasket and/or seal with the gas receiving open ends of the plurality of scan probes. The filter integrity testing apparatus 1 is positionable to a resting position, such as between rows of HEPA filters or in the space between an outer edge of the HEPA filter and an isolator wall or a HEPA filter assembly, that does not impinge the HEPA filter face.

FIG. 3 is a plan view of a filter integrity testing apparatus 1 described elsewhere herein mounted to an isolator HEPA filter assembly 210 comprising four HEPA filters 110A, 110B, 110C and 110D in a 2×2 filter grid arrangement. Each filter is mounted in a filter housing assembly (not depicted in FIG. 3) that surrounds the filter on all four sides.

In some embodiments, the filter sits within a filter housing assembly frame, the filter sealed to the frame with a flange along the edge of each side. In some embodiments a sealant and/or gasket may be used to inhibit or prevent the escape of air from around the filter edges. Any suitable sealant (e.g., a gel-type seal) for creating a seal that prevents air from escaping from around the filter edges may be used. The filter integrity testing apparatus 1 is mounted to the HEPA filter assembly 210 by the first end face 20 and the second end face 40. The filter integrity testing apparatus 1 is positioned relative to the HEPA filter assembly 210 such that the scan probe 10 gas receiving ends are located no more than about 2.5 cm from the outlet faces of the HEPA filters. The 2×2 filter grid defines a first row containing HEPA filters 110B and 110D and a second row containing HEPA filters 110A and 110C wherein the rows are separated by a distance defined by L1. The 2×2 filter grid further defines a first column containing HEPA filters 110A and 110B and a second column containing HEPA filters 110C and 110D wherein the columns are separated by a distance defined by L2. The automated mover 50 is movable along a length defined by the distance from the first end face 20 to the second end face 40. The automated mover is positioned between the HEPA filter columns, and the length of the automated mover 50 extends between the HEPA filter columns along a centerline between the HEPA filter columns. The first end face 20 is positioned past the outer edge of the first row of HEPA filters by a distance L3, and the second end face 40 is positioned past the outer edge of the second row of HEPA filters by a distance, L4. In FIG. 3, the scan module is depicted in resting position B. The scan module may also be located in resting position A or resting position C. The width of the automated mover 50 is less than the distance, L2, between the columns such that the automated mover does not impinge or otherwise obstruct the surface of any of HEPA filters 110A to 110D. The scan module 30 has a length that such that scan probe 10 gas receiving ends extend beyond the outer edge of each column of HEPA filters (including all edge gaskets and/or seals). The scan module 30 is movable along the length of the automated mover 50 in a first direction of travel D1 toward the first end face 20 and in a second direction of travel D2 toward the second end face 40. In some embodiments, the first direction of travel is essentially 180° opposed to the second direction of travel. The width of the scan module 30 is less than the distances L1, L3 and L4 such that the scan module 30 does not impinge or otherwise obstruct the surface of any of HEPA filters 110A to 110D at scan module 30 position A, B or C, respectively. Other HEPA filter matrixes not depicted in FIG. 3, such as, and without limitation, two columns and three rows of filters, three columns and two rows of filters, two columns and four rows of filters, and four columns and two rows of filters, are within the scope of the present disclosure.

FIG. 4 is a plan view of a filter integrity testing apparatus 1 described elsewhere herein mounted to an isolator HEPA filter assembly 210 comprising two HEPA filters 110A and 110B in a row arrangement. As described elsewhere herein, each filter is mounted in a filter housing (not depicted). The filter integrity testing apparatus 1 is mounted to the HEPA filter assembly 210 by the first end face 20 and the second end face 40. The filter integrity testing apparatus 1 is positioned relative to the HEPA filter assembly 210 such that the scan probe 10 gas receiving ends are located no more than about 2.5 cm from the outlet side faces of the HEPA filters. The HEPA filters are separated by a distance defined by L1. The automated mover 50 is movable along a length defined by the distance from the first end face 20 to the second end face 40. The length of the automated mover 50 is located along one edge of the column of HEPA filters and is positioned so that it does not impinge or otherwise obstruct the surface of HEPA filter 110A or 110B. The first end face 20 is positioned past the outer edge of HEPA filter 110B by a distance L3, and the second end face 40 is positioned past the outer edge of HEPA filter 110A by a distance, L4. The scan module 30 has a length such that scan probe 10 gas receiving ends 11 extend beyond the outer edge of each column of HEPA filters (including all edge seals). The scan module 30 is movable along the length of the automated mover 50 in a first direction of travel D1 toward the first end face 20 and in a second direction of travel D2 toward the second end face 40. In some embodiments, the first direction of travel is essentially 180° opposed to the second direction of travel. In FIG. 4, the scan module is depicted in position B. The scan module may also be located in position A or position B. The width of the scan module 30 is less than the distances L1, L3 and L4 such that the scan module 30 does not impinge or otherwise obstruct the surface of HEPA filter 110A or 110B at scan module 30 position A, B or C, respectively. Other HEPA filter matrixes not depicted in FIG. 3, such as one column of three filters, or a single filter, are within the scope of the present disclosure.

Scan module 30 positions A, B and C, depicted in FIGS. 3 and 4, or any other position where the filter integrity testing apparatus 1 does not impinge or otherwise obstruct the surface of a HEPA filter face, are suitable resting or parked positions when the filter integrity testing apparatus 1 is not in use. Such resting positions do not substantially interfere with normal isolator unidirectional air flow. Such resting positions further allow for HEPA filter access, such as for investigation, repair and/or replacement without removal of the filter integrity testing apparatus 1 from the isolator.

The gas discharge open end 12 of each scan probe 10 is operably connected to an aerosol detection apparatus by way of air suction line 60 tubing. Aerosol detection apparatuses are known in the art and are available commercially, for instance and without limitation, from Air Techniques International Model TDA 2G. In some embodiments, the tubing is thermoplastic tubing that is generally resistant to the effect of radiation and cleaning compounds, such as hydrogen peroxide vapor. In some embodiments of the disclosure, one aerosol detector is associated with a filter integrity testing apparatus 1. In such embodiments, operable connection of the scan probe air suction line 60 tubing to the aerosol detection apparatus may suitably be done by way of a manifold comprising an input from each scan probe and an output to the aerosol detection apparatus. In such an arrangement, the discharge end of air suction line 60 is operably connected to the input of a valve, and the output of the valve, in turn, is operably connected to the manifold as an input, such as by polymeric or metallic tubing. The manifold outlet is operably connected to the aerosol detection apparatus, such as by polymeric or metallic tubing. The manifold may optionally comprise an output valve positioned between the manifold and the aerosol detection apparatus. Manifold valve actuation between open and closed positions may be done manually or automatically.

In some embodiments, the filter integrity testing apparatus 1 and aerosol detection apparatus are integrated with an electronic control system. Electronic control systems are known in the art and include, without limitation, programmable logic controllers (PLC) and distributed control systems (DCS) having an operator interface. Filter integrity testing apparatus 1 scan probe 10 selection, scan module 30 movement rate, movement direction, and position may be controlled by the electronic control system. Scan module 30 position and movement rate may be suitably determined/measured by methods and devices known in the art, such as optical sensors and/or limit switches. Scan module 30 movement rate may suitably be controlled by varying air pressure in pneumatic cylinder embodiments or by varying motor speed in ball-screw embodiments. Scan module 30 movement direction may be suitably controlled by reversing the actuating air pressure in pneumatic cylinder embodiments or by reversing motor rotation in ball-screw embodiments. The electronic control system may also control air suction to individual scan probes 10, such as by actuation to open of a manifold input valve as described elsewhere herein.

The components of filter integrity testing apparatuses used in high radiation environments may be fabricated from materials that are radiation-insensitive in order to allow the apparatuses to be located in a radioactive environment without deterioration due to radiation. The materials are further resistant to vaporous hydrogen peroxide (VHP) that is used in isolator sanitization. For example, the automated mover may use electrical motors including resolver-based feedback, or may use pneumatics that are insensitive to radiation and VHP. Tubing may be made from a flexible radiation- and VHP-resistant polymer, such as polyurethane. Electrical cabling or other radiation-sensitive components may be insulated or coated with a radiation and VHP resistant polymer, such as polyurethane.

The present disclosure includes methods of determining the integrity of a HEPA filter. In some embodiments, a challenge aerosol such as DOP or PAO is introduced upstream from a first (inlet side) face of at least one HEPA filter as described elsewhere herein and the opposite (outlet side) face of the at least one HEPA filter is analyzed for integrity with a filter integrity testing apparatus 1 of the present disclosure as described elsewhere herein. In embodiments described elsewhere herein comprising a filter integrity testing apparatus 1, one aerosol detection apparatus, and a manifold, the entire face HEPA filter is scanned in multiple scans steps wherein only one scan probe is used in each step. In such embodiments, in a first step, a first scan probe 10 is selected by actuating the associated manifold input valve to the open position and actuating the remaining manifold input valves to the closed position. The scan module 30 is then automatically passed from a first resting position over the entire face of the HEPA filter to a second resting position thereby scanning the portion of the HEPA face and gasket and/or seal covered by the selected scan probe 10. During the scan, collected gas samples continuously pass out of the scan probe 10 discharge end 12 through air suction line 60 and to the aerosol detection apparatus where the samples are analyzed to determine the integrity of the HEPA filter. In a second step: (i) a second scan probe 10 is selected by actuating the associated manifold input valve to the open position and actuating the remaining manifold input valves to the closed position; and (ii) the scan module 30 is automatically passed in the opposite direction as compared to the first step, i.e., the second resting position to the first resting position thereby scanning the portion of the HEPA face covered by the scan probe 10 selected in the second step. This sequence of steps is continued until all of the scan probes 10 have been selected and passed over the entire surface of the HEPA filter face and the associated filter frame housing gaskets and/or seals.

Detection of aerosol vapor may trigger an operator interface notification, such as an indicator or an alarm. Upon notification of the presence of vapor, the automated scanning process mode may be stopped. In a manual control system mode, a desired scan probe 10 can be selected and the automated mover may be manually actuated to drive the scan module 30 to a desired location in order to investigate the source of any potential HEPA filter leak. Leak investigation may include drawing air samples through selected scan probe in order to precisely determine the location of the leak. Based on the methods herein, the location of the leak on the HEPA filter may be identified.

After the scan is complete, the scan module may be moved to a position that that does not impinge or otherwise obstruct the HEPA filter face. If a leak was detected, the HEPA filter may then be directly accessed for further investigation, servicing and/or replacement without removal of the filter integrity testing apparatus 1 from the isolator.

The HEPA filter integrity testing apparatus 1 of the present disclosure provides for a number of advantages.

The HEPA filter integrity testing apparatus 1 can be connected to any commercially available Aerosol Detection equipment (such as Air Techniques International Model TDA 2G).

The HEPA filter integrity testing apparatus 1 provides a consistent means for HEPA filter scanning within dangerous or limited-access environments, and provides automated scan probe 10 air suction line 60 switching, such that the entire filter face is tested. All testing can be performed with an operator located outside the isolator thereby eliminating operator exposure to unsafe conditions. If a leak is detected, via the control system, an operator has the ability to manually drive the device to any desired location for remote investigation of leaks, and to allow filter access during repairs or replacement.

The HEPA filter integrity testing apparatus 1 overcomes problems associated with manual HEPA filter testing. Such problems include: contacting and damaging the HEPA filter with the probe; rate of movement determination difficulty; difficulty in maintaining a maximum one inch distance from the filter face; difficulty in certifying that each manual stroke overlaps the previous stroke; and the need to remove and reinstall diffusion grids to perform testing.

The HEPA filter integrity testing apparatus 1 provides a way to test HEPA filters within small pharmaceutical isolators, including isolators where equipment blocks prolonged interior access.

The HEPA filter integrity testing apparatus 1 utilizes multiple probes in order to simplify movement complexity; movement is only performed in one dimension, while providing coverage of all required surfaces. By contrast, a single probe moved on X-Y coordinates requires greater control system complexity, with different hose management challenges.

One HEPA filter integrity testing apparatus 1 can scan multiple HEPA filter configurations, such as 1×2, 2×2, 2×3 and 2×4 grid patterns.

The HEPA filter integrity testing apparatus 1 scan module 30 resting position, such as at one end of a grid pattern or between HEPA filter rows in a grid pattern, allows for full access to the HEPA filter for replacement and repairs.

In isolators having HEPA filters in combination with a diffusion grid/membrane, the HEPA filter integrity testing apparatus 1 can be installed between the HEPA filter and diffusion grid/membrane and thereby operate without removal of the grid/membrane. Grid/membrane removal would only be required if a leak is detected and must be investigated.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A filter integrity testing apparatus, comprising:
an automated mover;
a scan module having a length and connected to the automated mover, the automated mover operable to move the scan module along an axis of travel, wherein the scan module length extends substantially perpendicular to the direction of travel; and
a plurality of scan probes disposed along the length of the scan module,
wherein each scan probe includes a gas receiving end and a gas discharge end wherein each scan probe is similarly oriented with respect to the gas receiving end and the gas discharge end, and the gas receiving end of each scan probe overlaps a gas receiving end of each adjacent scan probe, and wherein each scan probe has a length extending substantially perpendicular to the axis of travel.

2. The filter integrity testing apparatus of claim 1 wherein the automated mover defines a first end having a face and a second end having a face wherein a first mount is connected to the automated mover first end face and a second mount is connected to the second end face.

3. The filter integrity testing apparatus of claim 1 wherein the axis of travel includes an extension direction of travel and a retraction direction of travel disposed 180° from the extension direction of travel.

4. The filter integrity testing apparatus of claim 1 wherein the automated mover is a pneumatic cylinder or a motor-driven screw.

5. The filter integrity testing apparatus of claim 1 comprising an electronic control system in communication with the automated mover.

6. The filter integrity testing apparatus of claim 1 wherein each scan probe gas discharge end is operably connected to an aerosol detection apparatus.

7. An assembly, comprising
at least one HEPA filter mounted in a filter housing assembly, the HEPA filter having (i) a face defined by four edges and having a rectangular shape, (ii) a first edge of the face and a second edge of the face define a length of the HEPA filter face, and (iii) a third edge of the face and a fourth edge of the face define a width of the HEPA filter face, and
a filter integrity testing apparatus comprising (i) an automated mover, (ii) a scan module having a length and connected to the automated mover, the automated mover operable to move the scan module along an axis of travel, wherein the scan module length extends substantially perpendicular to the direction of travel, and (iii) a plurality of scan probes disposed along the length of the scan module,
wherein each scan probe includes a gas receiving end and a gas discharge end wherein each scan probe is similarly oriented with respect to the gas receiving end and the gas discharge end, and the gas receiving end of each scan probe overlaps a gas receiving end of each adjacent scan probe,
wherein each scan probe has a length extending substantially perpendicular to the axis of travel, and
wherein the automated mover defines a first end having a face and a second end having a face wherein a first mount is connected to the automated mover first end face and a second mount is connected to the second end face, wherein the filter integrity testing apparatus is coupled to the filter housing assembly by the first mount and the second mount, and
wherein the scan module is configured to sweep the complete length and width of the at least one HEPA filter face with the gas receiving ends of the plurality of scan probes.

8. The assembly of claim 7 wherein the filter integrity testing apparatus scan module is movable to a resting position that does not impinge the HEPA filter face.

9. The assembly of claim 7 wherein the axis of travel consists of an extension direction of travel and a retraction direction of travel essentially 180° opposed to the extension direction of travel.

10. The assembly of claim 7 wherein the automated mover is a pneumatic cylinder or a motor-driven screw.

11. The assembly of claim 7 comprising an electronic control system in communication with the automated mover.

12. The assembly of claim 7 wherein the gas receiving ends of the plurality of scan probes are positioned no more than about 2.5 cm from the filter face.

13. The assembly of claim 7 wherein each gas discharge end is operably connected to an aerosol detection apparatus.

14. The assembly of claim 7 comprising (i) a 2×2 matrix of HEPA filters defined by two rows and two columns of filters, (ii) a 2×3 matrix of HEPA filters defined by three rows and two columns of filters or (iii) a 2×4 matrix of HEPA filters defined by four rows and two columns of filters, each filter in a row of filters separated by a distance L1 and each filter in a column of filters separated by a distance L2,
wherein the width of the automated mover is less than L2 and the automated mover is positioned between the columns of filters along a centerline defined by a distance between the columns of filters of L2,
wherein the scan module has a length such that a scan probe extends beyond the outer edge of each column of HEPA filters, and wherein the scan module is further defined as having a width that is less than L1, and
wherein the resting position is: retracted; between the rows of filters in a 2×2 matrix; between the first and second rows of filters or between the second and third rows of filters in a 2×3 matrix; between the first and second rows of filters, between the second and third rows of filters, or between the third and fourth rows of filters in a 2×4 matrix; or extended.

15. A method of determining the integrity of a HEPA filter, the method comprising
(A) introducing a challenge aerosol upstream from a first face of at least one HEPA filter, the HEPA filter having (i) a face defined by four edges and having a rectangular shape, (ii) a first edge of the face and an associated gasket and/or seal and a second edge of the face and an associated gasket and/or seal define a length of the HEPA filter face, and (iii) a third edge of the face and an associated gasket and/or seal and a fourth edge of the face and an associated gasket and/or seal define a width of the HEPA filter face;
(B) analyzing the opposite face of the at least one HEPA filter for integrity with a filter integrity testing apparatus comprising (i) an automated mover, (ii) a scan module having a length and connected to the automated mover, the automated mover operable to move the scan module along an axis of travel, wherein the scan module length extends substantially perpendicular to the direction of travel, and (iii) a plurality of scan probes disposed along the length of the scan module,
wherein each scan probe includes a gas receiving end and a gas discharge end, each scan probe is similarly oriented with respect to the gas receiving end and the gas discharge end, and the gas receiving end of each scan probe overlaps a gas receiving end of each adjacent scan probe,
wherein each scan probe has a length extending substantially perpendicular to the axis of travel, and
wherein the scan module is configured such that the plurality of scan probes sweep the entire length and width of the HEPA filter face and associated gasket and/or seal;
(C) selecting a scan probe;
(D) moving the scan module across the entire HEPA filter face at a controlled rate sweeping the complete length of said face while continuously collecting gas samples therefrom with the selected scan probe receiving end and analyzing collected samples for the presence of aerosol with an aerosol detection apparatus operably connected to the scan probe gas discharge end to determine the integrity of a HEPA filter;

(E) deselecting the selected scan probe and selecting a scan probe that was not previously selected, and repeating step (D); and (F) repeating step (E) until all scan probes have been selected.

16. The method of claim 15 further comprising positioning the scan module to a resting position that does not impinge the HEPA filter face.

17. The method of claim 15 wherein the axis of travel consists of an extension direction of travel and a retraction direction of travel substantially 180° opposed to the extension direction of travel.

18. The method of claim 15 wherein the gas receiving ends of the plurality of scan probes are positioned no more than about 2.5 cm from the filter face.

19. The method of claim 15 comprising (i) a 2×2 matrix of HEPA filters defined by two rows and two columns of filters, (ii) a 2×3 matrix of HEPA filters defined by three rows and two columns of filters or (iii) a 2×4 matrix of HEPA filters defined by four rows and two columns of filters, each filter in a row of filters separated by a distance L1 and each filter in a column of filters separated by a distance L2, wherein the width of the automated mover is less than L2 and the automated mover is positioned to extend between the columns of filters along a centerline defined by a distance between the columns of filters of L2, wherein the scan module has a length that extends beyond the outer edge of each column of HEPA filters, and wherein the scan module is further defined as having a width that is less than L1, and wherein the resting position is: retracted; between the rows of filters in a 2×2 matrix; between the first and second rows of filters or between the second and third rows of filters in a 2×3 matrix; between the first and second rows of filters, between the second and third rows of filters, or between the third and fourth rows of filters in a 2×4 matrix; or extended.

* * * * *

UNITED STATES PATENT AND TRADEMARK OFFICE
CERTIFICATE OF CORRECTION

PATENT NO. : 10,180,384 B2
APPLICATION NO. : 15/409000
DATED : January 15, 2019
INVENTOR(S) : Verma et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 171 days.

Signed and Sealed this
Third Day of September, 2019

Andrei Iancu
*Director of the United States Patent and Trademark Office*